United States Patent [19]

Takahashi et al.

[11] Patent Number: 4,710,514
[45] Date of Patent: * Dec. 1, 1987

[54] FUNGICIDAL CARBAMATES AND THIOLCARBAMATES

[75] Inventors: Junya Takahashi; Toshiro Kato, both of Hyogo; Katsuzo Kamoshita, Osaka, all of Japan

[73] Assignee: Sumitomo Chemical Company, Limited, Osaka, Japan

[*] Notice: The portion of the term of this patent subsequent to Feb. 26, 2002 has been disclaimed.

[21] Appl. No.: 488,829

[22] Filed: Apr. 26, 1983

[30] Foreign Application Priority Data

May 4, 1982 [JP]   Japan ................................. 57-75766
May 4, 1982 [JP]   Japan ................................. 57-75767

[51] Int. Cl.$^4$ .................. A01N 47/20; C07C 125/073
[52] U.S. Cl. ..................... 514/485; 514/486; 558/239; 558/241; 558/392; 560/24; 560/29
[58] Field of Search ............... 560/24, 29, 33; 424/300; 260/465 D, 455 A; 514/485, 486; 558/393, 239, 241, 392

[56] References Cited

U.S. PATENT DOCUMENTS

| | | | |
|---|---|---|---|
| 2,946,768 | 7/1960 | Klauke et al. | 560/24 |
| 3,557,183 | 1/1971 | Ishiyama et al. | 260/465 D |
| 3,592,912 | 7/1971 | Ishiyama et al. | 424/304 |
| 3,933,470 | 1/1976 | Cross et al. | 71/111 |
| 4,325,966 | 4/1982 | Punja | 424/285 |
| 4,482,546 | 11/1984 | Takahashi et al. | 424/211 |
| 4,501,756 | 2/1985 | Nato et al. | 560/29 X |

FOREIGN PATENT DOCUMENTS

| | | |
|---|---|---|
| 2921130 | 12/1980 | Fed. Rep. of Germany . |
| 1507608 | 11/1967 | France . |
| 40-19103 | 8/1965 | Japan . |
| 7316502 | 1/1968 | Japan . |
| 389985 | 7/1965 | Switzerland . |

OTHER PUBLICATIONS

Chemical Abstracts 87:52961e.
"Antifungal Compounds", vol. 2, pp. 107–112.
Monatsch. Chem., Band. 57, pp. 63–70, (1931).
C. R. Acad. Sc. Paris, t. 289, S'erie D, pp. 691–693, (1979).

*Primary Examiner*—Dolph H. Torrence
*Attorney, Agent, or Firm*—Birch, Stewart, Kolasch & Birch

[57] ABSTRACT

A compound of the formula:

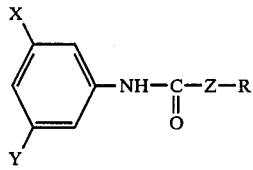

useful as a fungicidal agent against phytopathogenic fungi, particularly their strains resistant to benzimidazole, thiophanate and/or dicarboximide fungicides.

8 Claims, No Drawings

FUNGICIDAL CARBAMATES AND THIOLCARBAMATES

The present invention relates to fungicidal carbamate or thiolcarbamate derivatives, and to their fungicidal composition. It also relates to a processs for preparing the same.

Benzimidazole derivatives and thiophanate derivatives such as Benomyl (methyl 1-(butylcarbamoyl)benzimidazol-2-ylcarbamate), Fubelidazol (2-(2-furyl)benzimidazol Thiabendazole (2-(4-thiazolyl)benzimidazole), Carbendazim (methyl benzimidazol-2-ylcarbamate), Thiophanate-methyl (1,2-bis(3-methoxycarbonyl-2-thioureido)-benzene), Thiophanate (1,2-bis(3-ethoxycarbonyl-2-thioureido)benzene), 2-(O,S-dimethylphosphorylamino)-1-(3'-methoxycarbonyl-2'-thioureido)benzene and 2-(0,0-dimethylthiophosphorylamino)-1-(3'-methoxycarbonyl-2'-thioureido)-benzene are known to show an excellent fungicidal activity against various plant pathogenic fungi [cf. Antifungal Compounds, Vol. 2, p.107 edited by M. R. Siegel and H. D. Sisler], and they have been widely used as agricultural fungicides since 1970. However, their continuous application over a long period of time provides phytopathogenic fungi with tolerance to them, whereby their plant disease-preventive effect is much lowered. Further, the fungi which gained tolerance to some of the compounds also show considerable tolerance to some other kinds of derivatives. Thus, they are apt to obtain cross-tolerance. Therefore, if any material decrease of their plant disease-preventive effect is certain fields is observed, their application to such fields has to be discontinued. But, it is often observed that the density of drug-resistant organisms is not decreased even long after the discontinuation of the application. Although other kinds of fungicides have to be employed in such case, only few are so effective as these derivatives in controlling various phytopathogenic fungi. Dicarboximide fungicides such as Procymidone (3-(3',5'-di-chlorophenyl)-1,2-dimethylcyclopropane-1,2-dicarboximide), Iprodione (3-(3', 5'-dichlorophenyl)-1-isopropylcarbamoylimidazolidine-2,4-dione), Vinchlozoline (3-(3',5'-(dichlorophenyl)-5-methyl-5-vinyloxazolidin-2,4-dione), ethyl (RS)-3-(3',5'-dichlorophenyl)-5-methyl-2,4-dioxooxazolidine-5-carboxylate, etc. [cf. Crop Protection 1(2), 221–230 (1982)], which are effective against various plant diseases, particularly those caused by Botrytis cinerea, have the same defects as previously explained with respect to the benzimidazole and thiophanate derivatives.

In C.R. Acad. Sc. Paris, t. 289, S'erie D, pages 691–693 (1979), it is described that such herbicides as Barban (4-chloro-2-butynyl N-(3-chlorophenyl)carbamate), Chlorobufam (1-methyl-2-propynyl N-(3-chlorophenyl)carbamate), Chlorpropham (isopropyl N-(3-chlorophenyl)carbamate) and Propham (isopropyl N-phenylcarbamate) exhibit a fungicidal activity against certain organisms tolerant to some benzimidazole or thiophanate derivatives. However, their fungicidal activity against the drug-resistant fungi is not strong enough, and hence, practically they can not be used as fungicides.

As a result of the study seeking a new type of fungicides, it has now been found that anilides of the formula:

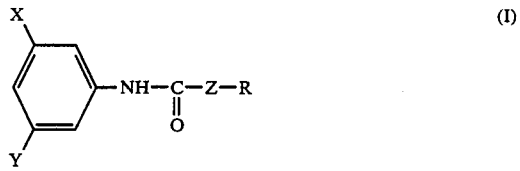

wherein X and Y are the same or different and each is a lower alkyl group or a lower alkoxy group, R is a lower alkyl group, a lower alkenyl group, a lower alkynyl group, a lower haloalkyl group, a lower haloalkenyl group, a lower haloalkynyl group or a lower alkyl group substituted with at least one member selected from the group consisting of cyano, lower alkoxy and lower cycloalkyl and Z is an oxygen atom or a sulfur atom, show an excellent fungicidal activity against plant pathogenic fungi which have developed resistance to the benzimidazole or thiophanate fungicides and/or dicarboximide fungicides. It is notable that their fungicidal potency against the organisms tolerant to the said known fungicides (hereinaftr referred to as "drug-resistant fungi" or "drug-resistant strains") is much higher than that against the organisms sensitive to the said known fungicides (hereinafter referred to as "drug-sensitive fungi" or "drug-sensitive strains").

The compounds of the formula (I) have not been disclosed in any literature or publication and novel compounds except methyl N-(3,5-dimethoxyphenyl)-carbamate, which is disclosed in Monatsch. Chem., Band 57, p.63–70 (1931), and methyl or ethyl N-(3,5-dimethylphenyl) carbamate, which is disclosed in U.S. Pat. No. 2,946,768. However, no biological activity of these compounds have been reported.

The term "lower" used hereinabove and hereinafter in connection with organic radicals or compounds indicates that such radicals or compounds each have not more than 6 carbon atoms.

The compounds of the formula (I) are fungicidally effective against a wide scope of plant pathogenic fungi, of which examples are as follows: Podosphaera leucotricha, Venturia inaegualis, Mycosphaerella pomi, Marssonina mali and Sclerotinia mali of apple, Phyllactinia kakicola and Gloeosporium kaki of persimmon, Cladosporium carpophilum and Phomopsis sp. of peach, Cercospora viticola, Uncinula necator, Elsinoe ampelina and Glomerella cingulata of grape, Cercospora beticola of sugarbeet, Cercospora arachidicola and Cercospora personata of peanut, Erysiphe graminis f. sp. hordei, Cercosporella herpotrichoides and Fusarium nivale of barley, Erysiphe graminis f. sp. tritici of wheat, Sphaerotheca fuliginea and Cladosporium cucumerinum of cucumber, Cladosporium fulvum of tomato, Corynespora melongenae of eggplant, Sphaerotheca humuli, Fusarium oxysporum f. sp. fragariae of strawberry, Botrytis alli of onion, Cercospora apii of cerely, Phaeoisariopsis griseola of kidney bean, Erysiphe cichoracearum of tobacco, Diplocarpon rosae of rose, Elsinoe fawcetti, Penicillium italicum, Penicillium digitatum of orange, Botrytis cinerea of cucumber, eggplant, tomato, strawberry, pimiento, onion, lettuce, grape, orange, cyclamen, rose or hop, Sclerotinia sclerotiorum of cucumber, eggplant, pimiento, lettuce, celery, kidney bean, soybean, azuki bean, potato or sunflower, Sclerotinia cinerea of peach or cherry, Mycosphaerella melonis of cucumber or melon, etc. Namely, the compounds of the formula (I)

are highly effective in controlling the drug-resistant strains of said fungi.

The compounds of the formula (I) are also fungicidally effective against fungi sensitive to said known fungicides as well as fungi to which said known fungicides are ineffective. Examples of such fungi are *Pyridularia oryzae, Pseudoperonospora cubensis, Plasmopara, viticola, Phytophthora infestans*, etc.

Advantageously, the compounds of the formula (I) are low in toxicity and have little detrimental actions on mammals, fishes and so on. Also, they may be applied to agricultural fields without causing any material toxicity to important crop plants.

Thus, the present invention provides a fungicidal composition which comprises, as an active ingredient, a fungicidally effective amount of the compound of the formula (I) and an inert carrier or diluent. It also provides a novel compound of the formula (I):

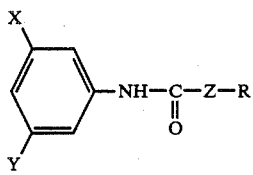
(I)

wherein X, Y, Z and R are each as defined above with the proviso that methyl N-(3,5-dimethoxyphenyl)carbamate is excluded. It also provides a combination composition comprising as an active ingredient a mixture of the compound of the formula (I) and at least one of the benzimidazole, thiophanate and dicarboximide fungicides, which composition is fungicidally effective against not only drug-sensitive fungi but also drug-resistant fungi, and hence particularly effective for the prevention of plant diseases. It also provides a method of controlling plant pathogenic fungi including drug-resistant strains and drug-sensitive strains applying a fungicidally effective amount of the compound of the formula (9I) to plant pathogenic fungi, and a process for producing the compound of the formula (I).

The compound of the formula (I) can be prepared by either one of the following procedures:

Procedure (a)

The compound of the formula (I) can be prepared by reacting a compound of the formula:

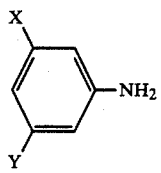
(II)

wherein X and Y are each as defined above, with a compound of the formula:

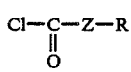
(III)

wherein Z and R are each as defined above.

The reaction is usually carried out in the presence of an inert solvent (e.g. benzene, toluene, tetrahydrofuran, chloroform, ethyl acetate, dimethylformamide). If desired, the reaction may be performed in the existence of a basic agent (e.g. pyridine, triethylamine, N,N-diethylaniline, sodium hydroxide, potassium hydroxide) so as to obtain the compound (I) in a high yield. The reaction may be accomplished at a temperature of 0° to 150° C. instantaneously or within 10 hours.

Procedure (b)

The compound of the formula (I) can be also prepared by reacting a compound of the formula:

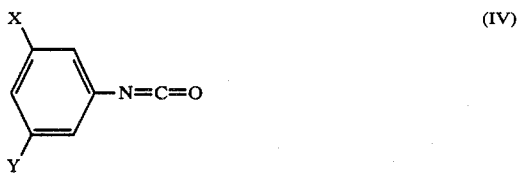
(IV)

wherein X and Y are each as defined above, with a compound of the formula:

R-Z-H    (V)

wherein R and Z are each as defined above.

The reaction is usually carried out in the absence or presence of an inert solvent (e.g. benzene, toluene, tetrahydrofuran, carbon tetrachloride). If desired, a catalyst (e.g. triethylamine, 1,4-diazabicyclo(2.2.2)octane) may be used. The reaction is normally accomplished at a temperature of 0° to 50° C. instantaneously or within 10 hours.

The starting compound (IV) in the procedure (b) is readily prepared by reacting a compound of the formula (II) with phosgene in an inert solvent (e.g. benzene, toluene, ethyl acetate, tetrahydrofuran) at a temperature of 50° C. to the boiling point of the solvent instantaneously or within 10 hours.

Some typical examples for preparation of the compound of the formula (I) is illustratively shown below.

EXAMPLE 1

Preparation of 1-methyl-2-propenyl N-[(3,5-dimethoxy)phenyl] carbamate according to Procedure (a):

3,5-Dimethoxyaniline (1.5 g) and N,N-diethylaniline (1.5 g) were dissolved in benzene (20 ml). To the resultant solution was dropwise added 1-methyl-2-propenyl chloroformate (1.4 g) in 5 minutes under ice-cooling. The resultant mixture was allowed to stand at room temperature for 12 hours, poured into ice-water and extracted with ethyl acetate. The extract was washed with water, dried over magnesium sulfate and concentrated under reduced pressure. The residue was purified by silica gel chromatography using toluene as the eluent to give 1-methyl-2-propenyl N-[(3,5-dimethoxy)phenyl] carbamate (2.1 g) in a yield of 88 %. $n^{21.0}_D$ 1.5359.

Elementary analysis: Calcd. for $C_{13}H_{17}NO_4$ C, 62.14 %; H, 6.82 %; N, 5.57 %. Found: C, 61.98 %; H, 6.52 N, 5.55 %.

EXAMPLE 2

Preparation of propargyl N-(3,5-dimethoxyphenyl)-carbamate according to Procedure (b):

A mixture of 3,5-dimethoxyaniline (1.5 g) in toluene (20 ml) was dropwise added to a toluene solution containing 10 g of phosgene at 10° to 20° C. The resulting mixture was gradually heated and, after being refluxed for 30 minutes, cooled to room temperature. The solvent was removed by distillation under reduced pressure to give 3,5-dimethoxyphenyl isocyanate (1.7 g). The thus obtained crude substance was added to a toluene solution (50 ml) containing triethylamine (1 g) and propargyl alcohol (2 g). The resultant mixture was allowed to stand at room temperature for 12 hours, poured into ice-water and extracted with ethyl acetate. The extract was washed with water, dried over magnesium sulfate and concentrated under reduced pressure. The residue was purified by recrystallization from toluene to give propargyl N-(3,5-dimethoxyphenyl)carbamate (1.7 g) in a yield of 75 % (calculated from the starting 3,5-dimethoxyaniline). M.P., 139.5°–140.5° C.

Elementary analysis: Calcd. for $C_{12}H_{13}NO_4$ N, 5.96 %; C, 61.27 %; H, 5.57 %. Found: N, 5.88 %; C, 61.33 H, 5.57 %.

In the similar manner, there can be prepared the compounds of the formula (I) as shown in Table 1.

TABLE 1

Formula (I): 3,5-disubstituted phenyl with X and Y substituents, bearing —NH—C(=O)—Z—R group.

| Compound No. | X | Y | Z | R | Physical constant |
|---|---|---|---|---|---|
| 1 | —CH₃ | —CH₃ | O | —CH(CH₃)₂ | M.P. 88.5–89° C. |
| 2 | —CH₃ | —CH₃ | O | —CH₂C≡CCH₂Cl | M.P. 86.5–87.5° C. |
| 3 | —OCH₃ | —OCH₃ | O | —CH(CH₃)₂ | $n_D^{23.5}$ 1.5300 |
| 4 | —OCH₃ | —OCH₃ | O | —CH(CH₃)—CH=CH₂ | $n_D^{21.0}$ 1.5359 |
| 5 | —OCH₃ | —OCH₃ | O | —CH₂C≡CH | M.P. 139.5–140.5° C. |
| 6 | —OCH₂ | —OCH₃ | O | —CH₂CH₂F | M.P. 98.5–100° C. |
| 7 | —OCH₃ | —OCH₃ | O | —CH₂CH=CHCH₂Cl | M.P. 46.5–48° C. |
| 8 | —OCH₃ | —OCH₃ | O | —CH₂C≡CCH₂Cl | M.P. 100.5–101° C. |
| 9 | —OCH₃ | —OCH₃ | O | —CH₂CH₂CN | M.P. 105–106° C. |
| 10 | —OCH₃ | —OCH₃ | O | —CH(CH₃)—CH(cyclopropyl) | $n_D^{21.0}$ 1.5326 |
| 11 | —OCH₃ | —OCH₃ | O | —CH(CH₂OCH₃)(CH₃) | $n_D^{21.0}$ 1.5229 |
| 12 | —OCH₃ | —OCH₃ | S | —CH(CH₃)₂ | M.P. 69–70.5° C. |
| 13 | —OC₂H₅ | —OC₂H₅ | O | —CH(CH₃)₂ | $n_D^{21.5}$ 1.5253 |

In the practical usage of the compounds of the formula (I) as fungicides, they may be applied as such or in a preparation form such as dusts, wettable powders, oil sprays, emulsifiable concentrates, tablets, granules, fine granules, aerosole or flowables. Such preparation forms can be prepared in a conventional manner by mixing at least one of the compounds of the formula (I) with an appropriate solid or liquid carrier(s) or diluent(s) and, if necessary, an appropriate adjuvant(s) (e.g. surfactants, adherents, dispersants, stabilizers) for improving the dispersibility and other properties of the active ingredient.

Examples of the solid carriers or diluents are botanical materials (e.g. flour, tobacco stalk powder, soybean powder, walnut-shell powder, vegetable powder, saw dust, bran, bark powder, cellulose powder, vegetable extract residue), fibrous materials (e.g. paper, corrugated cardboard, old rags), synthetic plastic powders, clays (e.g. kaolin, bentonite, fuller's earth), talcs, other inorganic materials (e.g. pyrophyllite, sericite, pumice, sulfur powder, active carbon) and chemical fertilizers (e.g. ammonium sulfate, ammonium phosphate, ammonium nitrate, urea, ammonium chloride).

Examples of the liquid carriers or diluents are water, alcohols (e.g. methanol, ethanol), ketones (e.g. acetone, methylethylketone), ethers (e.g. diethyl ether, dioxane, cellosolve, tetrahydrofuran), aromatic hydrocarbons (e.g. benzene, toluene, xylene, methyl naphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, carbon tetrachloride), etc.

Examples of the surfactants are alkyl sulfuric esters, alkyl sulfonates, alkylaryl sulfonates, polyethylene glycol ethers, polyhydric alcohol esters, etc. Examples of the adherents and dispersants may include cesein, gelatin, starch powder, carboxymethyl cellulose, gum arabic, alginic acid, lignin, bentonite, molasses, polyvinyl alcohol, pine oil and agar. As the stabilizers, there may be used PAP (isopropyl acid phosphate mixture), tricresyl phosphate (TCP), tolu oil, epoxydized oil, various surfactants, verious fatty acids and their esters, etc.

The foregoing preparations generally contain at least one of the compounds of the formulla (I) in a concentration of about 1 to 95 % by weight, preferably of 2.0 to 80 % by weight. By using the preparations, the compounds of the formula (I) are generally applied in such amounts as 2 to 100 g per 10 are.

When only the drug-resistant strains of phytopathogenic fungi are present, the compounds of the formula (I) may be used alone. However, when the drug-sensitive strains are present together with the drug-resistant strains, their alternate use with benzimidazole, thiophanate and/or dicarboximide fungicides or their combined use with benzimidazole, thiophanate and/or dicarboximide fungicides is favorable. In such alternate or combined use, each active ingredient may be employed as such or in conventional agricultural preparation forms. In case of the combined use, the weight proportion of the compounds of the formula (I) and the benzimidazole, thiophanate and/or dicarboximide fungicides may be from about 1 : 0.1 to 1 : 10.0.

Typical examples of the benzimidazole, thiophanate and dicarboximide fungicides are shown in Table 2.

TABLE 2

| Compound | Structure | Name |
| --- | --- | --- |
| A | benzimidazole with -NHCOOCH$_3$ at 2-position and -CONHC$_4$H$_9$(n) on N | Methyl-1-(butylcarbamoyl)benzimidazol-2-ylcarbamate |
| B | 2-(4-thiazolyl)benzimidazole | 2-(4-Thiazolyl)benzimidazole |
| C | benzimidazole-2-yl-NHCOOCH$_3$ | Methyl benzimidazol-2-ylcarbamate |
| D | 2-(2-furyl)benzimidazole | 2-(2-Furyl)benzimidazole |
| E | 1,2-benzene with two NHC(S)NHCOOCH$_3$ groups | 1,2-Bis(3-methoxycarbonyl-2-thioureido)benzene |
| F | 1,2-benzene with two NHC(S)NHCOOC$_2$H$_5$ groups | 1,2-Bis(3-ethoxycarbonyl-2-thioureido)benzene |

TABLE 2-continued

| Compound | Structure | Name |
|---|---|---|
| G | (structure) | 2-(O,S—Dimethylphosphorylamino)-1-(3'-methoxycarbonyl-2'-thioureido)benzene |
| H | (structure) | 2-(O,O—Dimethylthiophosphorylamino)-1-(3'-methoxycarbonyl-2'-thioureido)benzene |
| I | (structure) | N—(3',5'-Dichlorophenyl)-1,2-dimethylcyclopropane-1,2-dicarboximide |
| J | (structure) | 3-(3',5'-Dichlorophenyl)-1-isopropylcarbamoylimidazolidin-2,4-dione |
| K | (structure) | 3-(3',5'-Dichlorophenyl)-5-methyl-5-vinyloxazolidin-2,4-dione |
| L | (structure) | Ethyl (RS)—3-(3',5'-dichlorophenyl)-5-methyl-2,4-dioxo-oxazolidine-5-carboxylate |

Besides, the compounds of the formula (I) may be also used in admixture with other fungicides, herbicides, insecticides, miticides, fertilizers, etc.

When the compounds of the formula (I) are used as fungicides, they may be applied in such amounts as 2 to 100 grams per 10 ares. However, this amount may vary depending upon preparation forms, application times, application methods, application sites, diseases, crops and so on, and therefore, they are not limited to said particular amounts.

Some practical embodiments of the fungicidal composition according to the invention are illustratively shown in the following Examples wherein % and part(s) are by weight.

PREPARATION EXAMPLE 1

Two parts of Compound No. 4, 88 parts of clay and 10 parts of talc are thoroughly pulverized and mixed together to obtain a dust preparation containing 2 % of the active ingredient.

PREPARATION EXAMPLE 2

Thirty parts of Compound No. 5, 45 parts of diatomaceous earth, 20 parts of white carbon, 3 parts of sodium laurylsulfate as a wetting agent and 2 parts of calcium ligninsulfonate as a dispersing agent are mixed while being powdered to obtain a wettable powder preparation containing 30 % of the active ingredient.

PREPARATION EXAMPLE 3

Fifty parts of Compound No. 9, 45 parts of diatomaceous earth, 2.5 parts of calcium alkylbenzenesulfonate as a wetting agent and 2.5 parts of calcium ligninsulfonate as a dispersing agent were mixed while being powdered to obtain a wettable powder preparation containing 50 % of the active ingredient.

PREPARATION EXAMPLE 4

Ten parts of Compound No. 11, 80 parts of cyclohexanone and 10 parts of polyoxyethylene alkylaryl ether as an emulsifier were mixed together to obtain an emulsifiable concentrate preparation containing 10 % of the active ingredient.

PREPARATION EXAMPLE 5

One part of Compound No. 8, 1 part of Compound No. J, 88 parts of clay and 10 parts of talc were thoroughly pulverized and mixed together to obtain a dust preparation containing 2 % of the active ingredient.

PREPARATION EXAMPLE 6

Twenty parts of Compound No. 10, 10 parts of Compound K, 45 parts of diatomaceous earth, 20 parts of white carbon, 3 parts of sodium laurylsulfate as a wetting agent and 2 parts of calcium ligninsulfonate as a dispersing agent are mixed while being powdered to obtain a wettable powder preparation containing 30 % of the active ingredient.

PREPARATION EXAMPLE 7

Ten parts of Compound No. 12, 40 parts of Compound No. I, 45 parts of diatomaceous earth, 2.5 parts of calcium alkylbenzenesulfonate as a wetting agent and 2.5 parts of calcium ligninsulfonate as a dispersing agent were mixed while being powdered to obtain a wettable powder preparation containing 50 % of the active ingredient.

Typical test data indicating the excellent fungicidal activity of the compound of the formula (I) are shown below. The compounds used for comparison are as follows:

| Compound | Remarks |
| --- | --- |
| Control (a) 3-Cl-C$_6$H$_4$-NHCOCH$_3$ | Synthesized for comparison |
| Control (b) 4-Cl-C$_6$H$_4$-NHCOCH$_3$ | Synthesized for comparison |
| Control (c) 2-Cl-C$_6$H$_4$-NHCOCH$_3$ | Synthesized for comparison |
| Control (d) 3-Cl-C$_6$H$_4$-NHCOCH$_3$ | Synthesized for comparison |
| Control (e) 4-Cl-C$_6$H$_4$-NHCOC$_2$H$_5$ | Synthesized for comparison |
| Control (f) 2-Cl-C$_6$H$_4$-NHCOC$_2$H$_5$ | Synthesized for comparison |
| Control (g) 3-Br-C$_6$H$_4$-NHCOCH$_3$ | Synthesized for comparison |
| Control (h) 4-Br-C$_6$H$_4$-NHCOC$_2$H$_5$ | Synthesized for comparison |
| Control (i) 3,5-Cl$_2$-C$_6$H$_3$-NHCOCH(CH$_3$)$_2$ | Agricultural Biological Chemistry, 35, 1707–1719 (1971) |
| Control (j) 3,5-Cl$_2$-C$_6$H$_3$-NHCOCH$_2$CH=CH$_2$ | Agricultural Biological Chemistry, 35, 1707–1719 (1971) |
| Control (k) 3,5-Cl$_2$-C$_6$H$_3$-NHCOCH$_2$CH$_2$Cl | Agricultural Biological Chemistry, 35, 1707–1719 (1971) |
| Control (l) 3,5-Cl$_2$-C$_6$H$_3$-NHCOCH$_2$CN | Agricultural Biological Chemistry, 35, 1707–1719 (1971) |
| Swep 3,4-Cl$_2$-C$_6$H$_3$-NHCOCH$_3$ | Commercially available herbicide |
| Chlorpropham | Commercially available |

| Compound | | Remarks |
|---|---|---|
| 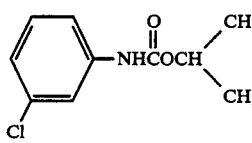 | | herbicide |
| Barban 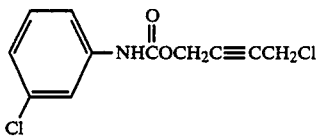 | | Commercially available herbicide |
| CEPC 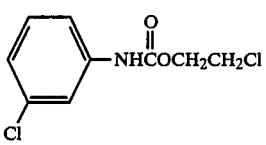 | | Commercially available herbicide |
| Propham 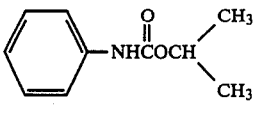 | | Commercially available herbicide |
| Chlorbufam 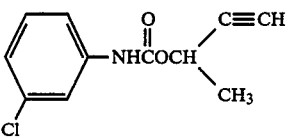 | | Commercially available herbicide |
| Benomyl 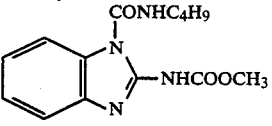 | | Commercially available fungicide |
| Thiophanate-methyl 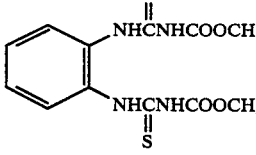 | | Commercially available fungicide |
| Carbendazim 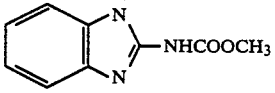 | | Commercially available fungicide |
| Thiabendazole 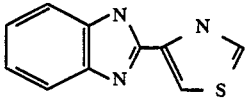 | | Commercially available fungicide |

EXPERIMENT 1

Protective activity test on powdery mildew of cucumber (*Sphaerotheca fuliginea*):

A flower pot of 90 ml volume was filed with sandy soil, and seeds of cucumber (var: Sagami-hanjiro) were sowed therein. Cultivation was carried out in a greenhouse for 8 days. Onto the resulting seedlings having cotyledons, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Sphaerotheca fuliginea* by spraying and further cultivated in the greenhouse. Ten days thereafter, the infectious state of the plants was observed. The degree of damage was determined in the following manner, and the results are shown in Table 3.

The leaves examined were measured for a percentage of infected area and classified into the corresponding disease indices, 0, 0.5, 1, 2, 4:

| Disease index | Percentage of infected area |
|---|---|
| 0 | No infection |
| 0.5 | Infected area of less than 5% |
| 1 | Infected area of less than 20% |
| 2 | Infected area of less than 50% |
| 4 | Infected area of not less than 50% |

The disease severity was calculated according to the following equation:

$$\text{Disease severity (\%)} = \frac{\Sigma \text{ (Disease index)} \times \text{(Number of leaves)}}{4 \times \text{(Total number of leaves examined)}} \times 100$$

The prevention value was calculated according to the following equation:

$$\text{Prevention value (\%)} = 100 - \frac{\text{(Disease severity in treated plot)}}{\text{(Disease severity in untreated plot)}} \times 100$$

TABLE 3

| Compound No. | Concentration of active ingredient (ppm) | Prevention value when inoculated with drug-resistant strain (%) | Prevention value when inoculated with drug-sensitive strain (%) |
|---|---|---|---|
| 4 | 200 | 100 | 0 |
| 7 | 200 | 100 | 0 |
| 8 | 200 | 100 | 0 |
| 9 | 200 | 100 | 0 |
| 10 | 200 | 100 | 0 |
| 11 | 200 | 100 | 0 |
| 12 | 200 | 100 | 0 |
| 13 | 200 | 100 | 0 |
| Control (a) | 200 | 0 | 0 |
| Control (b) | 200 | 0 | 0 |
| Control (c) | 200 | 0 | 0 |
| Control (d) | 200 | 0 | 0 |
| Control (e) | 200 | 0 | 0 |
| Control (f) | 200 | 0 | 0 |
| Control (g) | 200 | 0 | 0 |
| Control (h) | 200 | 0 | 0 |
| Control (i) | 200 | 0 | 0 |
| Control (j) | 200 | 0 | 0 |
| Control (k) | 200 | 0 | 0 |
| Control (l) | 200 | 0 | 0 |
| Chlorpropham | 200 | 0 | 0 |
| Barban | 200 | 25 | 0 |
| CEPC | 200 | 0 | 0 |
| Propham | 200 | 0 | 0 |
| Chlorbufam | 200 | 0 | 0 |
| Benomyl | 200 | 0 | 100 |
| Thiophanate- | 200 | 0 | 100 |

TABLE 3-continued

| Compound No. | Concentration of active ingredient (ppm) | Prevention value when inoculated with drug-resistant strain (%) | Prevention value when inoculated with drug-sensitive strain (%) |
| --- | --- | --- | --- |
| methyl Carbendazim | 200 | 0 | 100 |

As understood from the results shown in Table 3, the compounds of the formula (I) of the invention show an excellent preventive effect on the drug-resistant strain but do not show any preventive effect on the tested drug-sensitive strain. To the contrary, commercially available known fungicides such as Benomyl, Thiophanate-methyl and Carbendazim show a notable controlling effect on the drug-sensitive strain but not on the drug-resistant strain. Other tested compounds structurally similar to the compounds of the formula (I) do not show any fungicidal activity on the drug-sensitive strain and the drug-resistant strain.

EXPERIMENT 2

Preventive effect on cercospora leaf spot of sugarbeet (*Cercospora beticola*):

A flower pot of 90 ml volume was filled with sandy soil, and seeds of sugarbeet (var: Detroit dark red) were sowed therein. Cultivation was carried out in a greenhouse for 20 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Cercospora beticola* by spraying. The pot was covered with a polyvinyl chloride sheet to make a condition of high humidity, and cultivation was continued in the greenhouse for 10 days. The degree of damage was determined in the same manner as in Experiment 1, and the results are shown in Table 4.

TABLE 4

| Compound No. | Concentration of active ingredient (ppm) | Prevention value when inoculated with drug-resistant strain (%) | Prevention value when inoculated with drug-sensitive strain (%) |
| --- | --- | --- | --- |
| 4 | 200 | 100 | 0 |
| 5 | 200 | 100 | 0 |
| 6 | 200 | 97 | 0 |
| 7 | 200 | 94 | 0 |
| 8 | 200 | 100 | 0 |
| 9 | 200 | 98 | 0 |
| 10 | 200 | 98 | 0 |
| 11 | 200 | 100 | 0 |
| 12 | 200 | 100 | 0 |
| Control (a) | 200 | 0 | 0 |
| Control (b) | 200 | 0 | 0 |
| Control (c) | 200 | 0 | 0 |
| Control (d) | 200 | 0 | 0 |
| Control (e) | 200 | 0 | 0 |
| Control (f) | 200 | 0 | 0 |
| Control (g) | 200 | 0 | 0 |
| Control (h) | 200 | 0 | 0 |
| Control (i) | 200 | 0 | 0 |
| Control (j) | 200 | 0 | 0 |
| Control (k) | 200 | 0 | 0 |
| Control (l) | 200 | 0 | 0 |
| Chlorpropham | 200 | 0 | 0 |
| Barban | 200 | 25 | 0 |
| CEPC | 200 | 0 | 0 |
| Propham | 200 | 0 | 0 |
| Chlorbufam | 200 | 0 | 0 |
| Benomyl | 200 | 0 | 100 |
| Thiophanate-methyl | 200 | 0 | 100 |
| Carbendazim | 200 | 0 | 100 |

As understood from the results shown in Table 4, the compounds of the formula (I) of the invention show an excellent preventive effect on the drug-resistant strain but do not show any preventive effect on the tested drug-sensitive strain. To the contrary, commecially available known fungicides such as Benomyl and Thiophanate-methyl show notable controlling effect on the drug-sensitive strain but not on the drug-resistant strain. Other tested compounds structurally similar to the compounds of the formula (I) do not show any fungicidal activity on the drug-sensitive strain and the drug-resistant strain.

EXPERIMENT 3

Preventive effect on scab of pear (*Venturia nashicola*):

A plastic pot of 90 ml volume was filled with sandy soil, and seeds of pear (var: Chojuro) were sowed therein. Cultivation was carried out in a greenhouse for 20 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Venturia nashicola* by spraying. The resulting plants were placed at 20° C. under a condition of high humidity for 3 days and then at 20° C. under irradiation with a fluorescent lamp for 20 days. The degree of damage was determined in the same manner as in Experiment 1, and the results are shown in Table 5.

TABLE 5

| Compound No. | Concentration of active ingredient (ppm) | Prevention value when inoculated with drug-resistant strain (%) | Prevention value when inoculated with drug-sensitive strain (%) |
| --- | --- | --- | --- |
| 1 | 200 | 94 | 0 |
| 2 | 200 | 94 | 0 |
| 3 | 200 | 97 | 0 |
| 4 | 200 | 100 | 0 |
| 5 | 200 | 100 | 0 |
| 8 | 200 | 100 | 0 |
| 9 | 200 | 100 | 0 |
| 10 | 200 | 97 | 0 |
| 11 | 200 | 100 | 0 |
| 12 | 200 | 100 | 0 |
| Benomyl | 200 | 0 | 100 |
| Thiophanate-methyl | 200 | 0 | 100 |

As understood from the results shown in Table 5, the compounds of the formula (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

EXPERIMENT 4

Preventive effect on brown leaf-spot of peanut (*Cercospora arachidicola*):

A plastic pot of 90 ml volume was filled with sandy soil, and seeds of peanut (var: Chiba hanryusei) were sowed therein. Cultivation was carried out in a greenhouse for 14 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Cercospora arachidicola* by spraying. The resulting plants were covered with a polyvinyl chloride sheet to make a condition of humidity and cultivated in the greenhouse for 10 days. The degree of damage was determined in the same manner as in Experiment 1, and the results are shown in Table 6.

TABLE 6

| Compound No. | Concentration of active ingredient (ppm) | Prevention value when inoculated with drug-resistant strain (%) | Prevention value when inoculated with drug-sensitive strain (%) |
| --- | --- | --- | --- |
| 4 | 200 | 100 | 0 |
| 8 | 200 | 100 | 0 |
| 11 | 200 | 100 | 0 |
| 12 | 200 | 100 | 0 |
| 13 | 200 | 97 | 0 |
| Benomyl | 200 | 0 | 100 |
| Thiophanate-methyl | 200 | 0 | 100 |

As understood from the results shown in Table 6, the compounds of the formula (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

EXPERIMENT 5

Preventive effect on gray mold of cucumber (*Botrytis cinerea*):

Plastic pots of 90 ml volume was filled with sandy soil, and seeds of cucumber (var: Sagami-hanjiro) were sowed therein. Cultivation was carried out in a greenhouse for 8 days to obtain cucumber seedlings expanding cotyledons. Onto the resulting seedlings, the test compound formulated in emulsifiable concentrate or wettable powder and diluted with water was sprayed at a rate of 10 ml per pot. After air-drying, the seedlings were inoculated with mycelial disks (5 mm in diameter) of the drug-resistant or drug-sensitive strain of *Botrytis cinerea* by putting them on the leaf surfaces. After the plants were infected by incubating under high humidity at 20° C. for 3 days, the rates of disease severity were observed. The degree of damage was determined in the same manner as in Experiment 1, and the results are shown in Table 7.

TABLE 7

| Compound No. | Concentration of active ingredient (ppm) | Prevention value when inoculated with drug-resistant strain (%) | Prevention value when inoculated with drug-sensitive strain (%) |
| --- | --- | --- | --- |
| 1 | 200 | 98 | 0 |
| 2 | 200 | 98 | 0 |
| 3 | 200 | 100 | 0 |
| 4 | 200 | 100 | 0 |
| 5 | 200 | 98 | 0 |
| 6 | 200 | 94 | 0 |
| 7 | 200 | 94 | 0 |
| 8 | 200 | 100 | 0 |
| 9 | 200 | 98 | 0 |
| 10 | 200 | 98 | 0 |
| 11 | 200 | 100 | 0 |
| 12 | 200 | 100 | 0 |
| 13 | 200 | 98 | 0 |
| Benomyl | 200 | 0 | 100 |
| Thiophanate-methyl | 200 | 0 | 100 |
| Thiabendazole | 200 | 0 | 100 |

As understood from the results shown in Table 7, the compounds of the formula (I) of the invention show an excellent preventive effect on the drugresistant strain but do not show any preventive effect on the tested drug-sensitive strain. To the contrary, commercially available known fungicides such as Benomyl, Thiophanate-methyl and Carbendazim show a notable controlling effect on the drug-sensitive strain but not on the drug-resistant strain.

EXPERIMENT 6

Preventive effect on gummy stem blight of cucumber (*Mycosphaerella melonis*):

Plastic pots of 90 ml volume was filled with sandy soil, and seeds of cucumber (var: Sagami-hanjiro) were sowed therein. Cultivation was carried out in a greenhouse for 8 days to obtain cucumber seedlings expanding cotyledons. Onto the resulting seedlings, the test compound formulated in emulsifiable concentrate or wettable powder and diluted with water were sprayed at a rate of 10 ml per pot. After air-drying, the seedlings were inoculated with a mycelial disks (5 mm in diameter) of the drug-resistant or drug-sensitive strain of *Mycosphaerella melonis* by putting them on the leaf surfaces. After the plants were infected by incubating under high humidity at 25° C. for 4 days, the rates of disease severity were observed. The degree of damage was determined in the same manner as in Experiment 1, and the results are shown in Table 8.

TABLE 8

| Compound No. | Concentration of active ingredient (ppm) | Prevention value when inoculated with drug-resistant strain (%) | Prevention value when inoculated with drug-sensitive strain (%) |
| --- | --- | --- | --- |
| 4 | 200 | 100 | 0 |
| 8 | 200 | 100 | 0 |
| 11 | 200 | 100 | 0 |
| 12 | 200 | 100 | 0 |
| Benomyl | 200 | 0 | 100 |
| Thiophanate-methyl | 200 | 0 | 100 |

As understood from the results shown in Table 8, the compounds of the formula (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

EXPERIMENT 7

Preventive effect on green mold of orange (*Penicillium italicum*): Fruits of orange (var: Unshu) were washed with water and dried in the air. The fruits were immersed in a solution of the test compound prepared by diluting an emulsifiable concentrate comprising the test compound with water for 1 minute. After drying in the air, the fruits were inoculated with a spore suspension of the drug-resistant or drug-sensitive strain of *Penicillium italicum* by spraying and placed in a room of high humidity for 14 days. The degree of damage was determined in the following manner:

The fruits examined were measured for a percentage of infected area and classified into the corresponding indices, 0, 1, 2, 3, 4, 5:

| Disease index | Percentage of infected area |
| --- | --- |
| 0 | No infection |
| 1 | Infected area of less than 20% |
| 2 | Infected area of less than 40% |
| 3 | Infected area of less than 60% |
| 4 | Infected area of less than 80% |
| 5 | Infected area of not less than 80% |

Calculation of the degree of damage and the prevention value was made as in Experiment 1.

The results are shown in Table 9.

TABLE 9

| Compound No. | Concentration of active ingredient (ppm) | Prevention value when inoculated with drug-resistant strain (%) | Prevention value when inoculated with drug-sensitive strain (%) |
| --- | --- | --- | --- |
| 1 | 200 | 88 | 0 |
| 2 | 200 | 94 | 0 |
| 6 | 200 | 97 | 0 |
| 11 | 200 | 100 | 0 |
| 12 | 200 | 100 | 0 |
| Benomyl | 200 | 0 | 100 |
| Thiophanate-methyl | 200 | 0 | 100 |

As understood from the results shown in Table 9, the compounds of the formula (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

EXPERIMENT 8

Phytotoxicity on crop plants:

Plastic pots of 150 ml volume were filled with sandy soil, and seeds of wheat (var: Norin No. 61), apple (var: Kogyoku) and peanut (var: Chiba banryusei) were sowed therein. Cultivation was carried out in a greenhouse. Onto the resulting seedlings, the test compound formulated in emulsifiable concentrate or wettable powder and diluted with water was sprayed. After cultivation in the greenhouse for additional 10 days, the phytotoxicity was examined on the following criteria:

| Extent | Observation |
| --- | --- |
| − | No abnormality |
| + | Abnormality due to phytotoxicity observed in a part of crop plants |
| + + | Abnormality due to phytotoxicity observed in entire crop plants |
| + + + | Crop plants withered due to phytotoxicity |

The results are shown in Table 10.

TABLE 10

| Compound No. | Concentration of active ingredient (ppm) | Phytotoxicity Wheat | Phytotoxicity Apple | Phytotoxicity Peanut |
| --- | --- | --- | --- | --- |
| 1 | 1000 | − | − | − |
| 4 | 1000 | − | − | − |
| 11 | 1000 | − | − | − |
| Barban | 1000 | − | + + | + + |
| CEPC | 1000 | − | + + | + + |
| Swep | 1000 | + + | + + | + |

As understood from the results shown in Table 10, the compounds of the formula (I) of the invention produce no material phytotoxicity, while commercially available herbicides having a chemical structure similar thereto produce considerable phytotoxicity.

EXPERIMENT 9

Preventive effect on powdery mildew of cucumber (*Sphaerotheca fuliginea*):

A plastic pot of 90 ml volume was filled with sandy soil, and seeds of cucumber (var: Sagami-hanjiro) were sowed therein. Cultivation was carried out in a greenhouse for 8 days. Onto the resulting seedlings having cotyledons, the test compound(s) formulated in emulsifiable concentrate or wettable powder and diluted with water were sprayed at a rate of 10 ml per pot. Then, the seedlings were inoculated with a mixed spore suspension of the drug-resistant and drug-sensitive strain of *Sphaerotheca fuliginea* by spraying and further cultivated in the greenhouse. Ten days thereafter, the infectious state of the plants was observed. The degree of damage was determined in the same manner as in Experiment 1, and the results are shown in Table 11.

TABLE 11

| Compound No. | Concentration of active ingredient (ppm) | Prevention value (%) |
| --- | --- | --- |
| 4 | 100 | 42 |
| 4 | 20 | 0 |
| 5 | 100 | 38 |
| 5 | 20 | 0 |
| 7 | 100 | 36 |
| 7 | 20 | 0 |
| 8 | 100 | 44 |
| 8 | 20 | 0 |
| 11 | 100 | 42 |
| 11 | 20 | 0 |
| A | 100 | 42 |
| A | 20 | 10 |
| B | 500 | 42 |
| B | 100 | 8 |
| C | 100 | 42 |
| C | 20 | 10 |
| D | 500 | 34 |
| D | 100 | 0 |
| E | 100 | 44 |
| E | 20 | 8 |
| F | 100 | 42 |
| F | 20 | 6 |

TABLE 11-continued

| Compound No. | Concentration of active ingredient (ppm) | Prevention value (%) |
|---|---|---|
| G | 100 | 42 |
| G | 20 | 8 |
| H | 100 | 40 |
| H | 20 | 5 |
| 4 + A | 20 + 20 | 100 |
| 4 + F | 20 + 20 | 100 |
| 5 + A | 20 + 20 | 100 |
| 5 + B | 20 + 20 | 100 |
| 5 + C | 20 + 20 | 100 |
| 5 + D | 20 + 20 | 100 |
| 7 + G | 20 + 20 | 100 |
| 7 + H | 20 + 20 | 100 |
| 8 + A | 20 + 20 | 100 |
| 8 + B | 20 + 20 | 100 |
| 8 + E | 20 + 20 | 100 |
| 8 + F | 20 + 20 | 100 |
| 11 + A | 20 + 20 | 100 |
| 11 + E | 20 + 20 | 100 |

As understood from the results shown in Table 11, the combined use of the compounds of the formula (I) of the invention with benzimidazole, thiophanate and/or dicarboximide fungicides show much more excellent preventive effect than their sole use.

EXPERIMENT 10

Preventive effect on gray mold of tomato (*Botrytis cinerea*):

A plastic pot of 90 ml volume was filled with sandy soil, and seeds of tomato (var: Fukuji No. 2) were sowed therein. Cultivation was carried out in a greenhouse for 4 weeks. Onto the resulting seedlings at the 4-leaf stage, the test compound(s) formulated in emulsifiable concentrate or wettable powder and diluted with water were sprayed at a rate of 10 ml per pot. Then, the seedlings were inoculated with a mixed spore suspension of the drug-resistant and drug-sensitive strain of *Botrytis cinerea* by spraying and placed at 20° C. in a room of high humidity for 5 days. The degree of damage was determined in the same manner as in Experiment 1, and the results are shown in Table 12.

TABLE 12

| Compound No. | Concentration of active ingredient (ppm) | Prevention value (%) |
|---|---|---|
| 4 | 50 | 42 |
| 4 | 10 | 0 |
| 6 | 50 | 32 |
| 6 | 10 | 0 |
| 9 | 50 | 36 |
| 9 | 10 | 0 |
| 10 | 50 | 44 |
| 10 | 10 | 0 |
| 12 | 50 | 42 |
| 12 | 10 | 0 |
| I | 100 | 46 |
| I | 20 | 16 |
| J | 100 | 42 |
| J | 20 | 14 |
| K | 100 | 40 |
| K | 20 | 8 |
| L | 100 | 38 |
| L | 20 | 8 |
| 4 + I | 10 + 20 | 100 |
| 4 + J | 10 + 20 | 100 |
| 4 + K | 10 + 20 | 100 |
| 4 + L | 10 + 20 | 100 |
| 6 + I | 10 + 20 | 100 |
| 6 + K | 10 + 20 | 100 |
| 9 + I | 10 + 20 | 100 |
| 9 + L | 10 + 20 | 100 |
| 10 + I | 10 + 20 | 100 |
| 10 + J | 10 + 20 | 100 |
| 12 + I | 10 + 20 | 100 |
| 12 + K | 10 + 20 | 100 |

As understood from the results shown in Table 12, the combined use of the compounds of the formula (I) of the invention with benzimidazole, thiophanate and/or dicarboximide fungicides show much more excellent preventive effect than their sole use.

What is claimed is:

1. A compound of the formula:

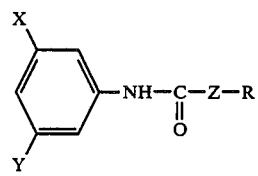

wherein X and Y are the same or different and each is a lower alkyl group or a lower alkoxy group, R is a lower alkenyl group, a lower alkynyl group, a lower haloalkyl group, a lower haloalkenyl group, a lower haloalkynyl group or a lower alkyl group substituted with at least one member selected from the group consisting of beta-cyano, lower alkoxy and lower cycloalkyl and Z is an oxygen atom or a sulfur atom.

2. A compound of the formula:

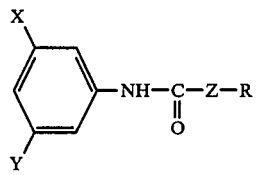

wherein X and Y are the same or different and each is a lower alkyl group or a lower alkoxy group, R is a lower alkenyl group, a lower alkynyl group, a lower haloalkyl group, a lower haloalkenyl group, a lower haloalkynyl group or a lower alkyl group substituted with at least one member selected from the group consisting of cyano, lower alkoxy and lower cycloalkyl and Z is an oxygen atom or a sulfur atom, with the proviso that R is not alpha-cyanoethyl.

3. A compound according to claim 2, wherein X is methyl, methoxy or ethoxy, Y is methyl, methoxy or ethoxy and R is a group of the formula, $$-CH_2C{\equiv}CCH_2Cl, \quad -\underset{\underset{CH_3}{|}}{CH}-CH{=}CH_2, \quad -CH_2C{\equiv}CH,$$

$$-CH_2CH_2F, \quad -CH_2CH{=}CHCH_2Cl, \quad -CH_2CH_2CN,$$

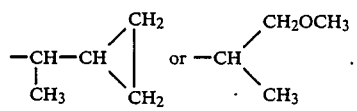

4. A fungicidal composition which comprises as an active ingredient a fungicidally effective amount of a compound of the formula:

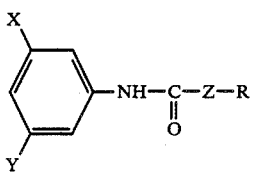

wherein X and Y are the same or different and each is a lower alkyl group or a lower alkoxy group, R is an isopropyl group, a lower alkenyl group, a lower alkynyl group, a lower haloalkyl group, a lower haloalkenyl group, a lower haloalkynyl group or a lower alkyl group substituted with at least one member selected from the group consisting of beta-cyano, lower alkoxy and lower cycloalkyl and Z is an oxygen atom or a sulfur atom, and an inert carrier or diluent.

5. A fungicidal composition according to claim 4, wherein X is methyl, methoxy or ethoxy, Y is methyl, methoxy or ethoxy and R is a group of the formula

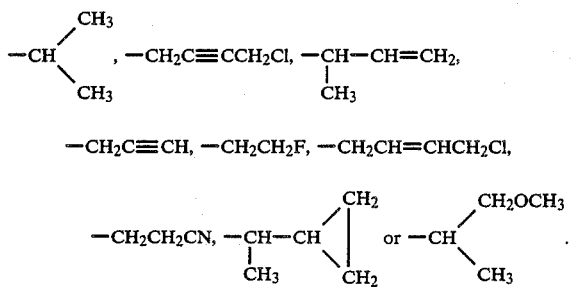

6. A fungicidal composition which comprises as an active ingredient a fungicidally effective amount of a compound of the formula:

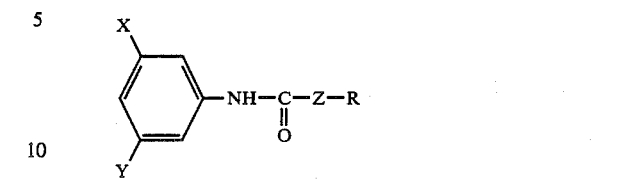

wherein X and Y are the same or different and each is a lower alkyl group or a lower alkoxy group, R is an isopropyl group, a lower alkenyl group, a lower alkynyl group, a lower haloalkyl group, a lower haloalkenyl group, a lower haloalkynyl group or a lower alkyl group substituted with at least one member selected from the group consisting of cyano, lower alkoxy and lower cycloalkyl and Z is an oxygen atom or sulfur atom, with the proviso that R is not alpha-cyanoethyl, and an inert carrier or diluent.

7. A fungicidal composition according to claim 6, wherein X is methyl, methoxy or ethoxy, Y is methyl, methoxy or ethoxy and R is a group of the formula

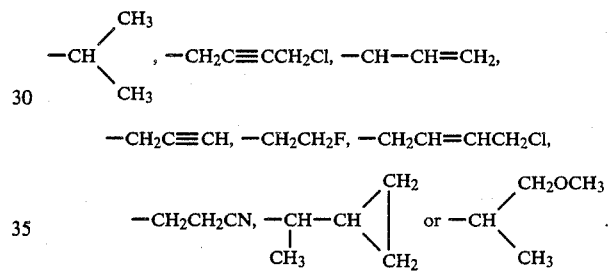

8. A fungicidal composition according to claim 7, wherein Z is O.

* * * * *